US 8,151,190 B2
Apr. 3, 2012

(12) United States Patent
Taki et al.

(10) Patent No.: US 8,151,190 B2
(45) Date of Patent: Apr. 3, 2012

(54) ANALYSIS DEVICE

(75) Inventors: Miki Taki, Hitachinaka (JP); Yoshimitsu Takagi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 716 days.

(21) Appl. No.: 11/498,900

(22) Filed: Aug. 4, 2006

(65) Prior Publication Data

US 2007/0038411 A1 Feb. 15, 2007

(30) Foreign Application Priority Data

Aug. 5, 2005 (JP) ................................. 2005-227771

(51) Int. Cl.
*G06F 15/00* (2006.01)
(52) U.S. Cl. ....................................... 715/705; 702/182
(58) Field of Classification Search .................. 715/705, 715/708; 702/182
See application file for complete search history.

(56) References Cited

U.S. PATENT DOCUMENTS

| 5,481,667 A | 1/1996 | Bieniek et al. | |
| 5,513,308 A * | 4/1996 | Mori | 715/707 |
| 5,805,465 A * | 9/1998 | Itoh | 702/182 |
| 6,134,644 A | 10/2000 | Mayuzumi et al. | |
| 2002/0031444 A1 * | 3/2002 | Ito et al. | 422/62 |
| 2002/0144192 A1 | 10/2002 | Owari | |
| 2004/0002841 A1 * | 1/2004 | Mayuzumi et al. | 703/7 |
| 2006/0050302 A1 * | 3/2006 | Sawaguchi | 358/1.15 |
| 2007/0032968 A1 * | 2/2007 | Nakamura | 702/56 |

FOREIGN PATENT DOCUMENTS

| JP | 4-349526 A | 12/1992 |
| JP | 5-88832 | 4/1993 |
| JP | 6-148197 | 5/1994 |
| JP | 2000-12605 | 4/2000 |
| JP | 2000-266754 | 9/2000 |

* cited by examiner

*Primary Examiner* — Chat Do
*Assistant Examiner* — Andrea C Leggett
(74) *Attorney, Agent, or Firm* — Mattingly & Malur, PC

(57) ABSTRACT

An analysis device allowing any person to utilize job guidance for setting and assignment operations with high efficiency regardless of a level of skill in an automatic analysis device which has a complicated screen configuration with an increase of functions. A storage unit stores a job guidance file and a correspondence list file indicating correspondences between procedure IDs, codes, buttons, etc. in the job guidance file and screen IDs for device control program software. When an operator selects the procedure ID or the like in a displayed job guidance window, control is performed such that the screen ID corresponding to the selected procedure ID or the like is searched for in the correspondence list file, and the displayed screen is shifted to one corresponding to the searched screen ID for the device control program software.

7 Claims, 11 Drawing Sheets

FIG.3

EXAMPLE OF CORRESPONDENCE LIST FILE FOR SHIFTING FROM SCREEN BASED ON DEVICE CONTROL PROGRAM SOFTWARE TO OPERATION GUIDANCE WINDOW

| JOB MENU | SUB-JOB MENU | WINDOW | SCREEN ID | HELP FILE ID |
|---|---|---|---|---|
| WORKPLACE JOB | TEST SELECTION | BASE | HD¥Workpl | A_1.html |
| | | DEMOGRAPHICS | HD¥Work¥Demo | A_1_1.html |
| | | REPEAT | HD¥Work¥ts | A_1_2.html |
| | | RERUN ASSIGNMENT | HD¥Work¥rerun | A_1_3.html |
| | DATA REVIEW | SEARCH | HD¥Work¥search | A_2_1.html |
| | | DETAILED REVIEW | HD¥Work¥detail | A_2_2.html |
| ... | ... | ... | ... | ... |

FIG. 4

EXAMPLE OF CORRESPONDENCE LIST FILE FOR SHIFTING FROM PROCEDURE ID IN MANUAL TO SCREEN BASED ON DEVICE CONTROL PROGRAM SOFTWARE

⟨SHIFT TO ONE SCREEN⟩

| NAME OF PROCEDURE | PROCEDURE ID IN MANUAL | SCREEN ID |
|---|---|---|
| RERUN RACK ASSIGNMENT | Rerun_Rack_regist | HD¥Work¥rerun |
| REAGENT PRIME | Mainte_reagent | HD¥Mainte. |
| ... | ... | ... |

FIG. 8

EXAMPLE OF CORRESPONDENCE LIST FILE FOR SHIFTING FROM PROCEDURE ID IN MANUAL TO SCREEN BASED ON DEVICE CONTROL PROGRAM SOFTWARE

⟨SHIFT TO PLURAL SCREENS⟩

| NAME OF PROCEDURE | SUB-DEVISION OF PROCEDURE | PROCEDURE ID IN MANUAL | GROUP ID | SCREEN ID |
|---|---|---|---|---|
| CONTROL | CONTROL ASSIGNMENT | QC_Control_regist | HD¥Gr_A1 | HD¥QC¥Setting |
| | ASSIGNMENT WINDOW | | | HD¥QC¥Setting¥Regist |
| | TARGET VALUE ENTRY | | | HD¥QC¥Install |
| | RACK POSITION ASSIGNMENT | | | HD¥QC¥Control¥Regist |

ANALYSIS DEVICE

BACKGROUND OF THE INVENTION

1. Field of the Invention

The present invention relates to an analysis device for analyzing or counting component concentration and/or population, and more particularly to an analysis device for carrying out a job over a plurality of operational screens.

2. Description of the Related Art

In many of known analysis devices, dedicated consoles are provided and control program software is used to control input/output of various kinds of information including operational screens. Recently, a method of installing control program software, which controls an analysis section, in a universal personal computer has been primarily employed. With an increase of functions performed in the analysis device, the control program software requires an operator to manipulate a larger number of operational screens.

When a screen configuration is divided per object, the control program software has problems as follows. When there are many operational screens to be manipulated, the number of steps until reaching a target screen through screen shift (transition) is so increased as to make skilled operators feel troublesome, and a longer time is taken for screen setting. Further, because a quantity of information displayable on one screen is small, it is harder to confirm the entire screen configuration.

On the other hand, in the case of a hierarchical screen configuration to display the overall makeup of operational screens, a beginner or an operator temporarily using the control program software is often embarrassed at starting the setting from which one of the operational screens. In particular, when condition setting parameters and information necessary for performing analysis are inputted over a plurality of operational screens, there is a problem of requiring a longer time for setting until start of the intended operation. Thus, in the analysis device having various and complicated functions, those problems cannot be overcome by an improvement of only the screen configuration in many cases because of the need of displaying a large number of matters.

With the view of overcoming the above-described problems, Patent Document 1 (JP,A 2000-266754) discloses an automatic analysis device capable of displaying a job menu for navigation or of changing the displayed contents depending on an operator's level. Also, Patent Document 2 (JP,A 5-88832) discloses a technique for changing the contents displayed on job guide screens depending on a level of skill. Further, Patent Document 3 (JP,A 6-148197) discloses a technique enabling a user to set and construct desired operational screens from among a plurality of screens.

However, the techniques disclosed in Patent Documents 1 and 2 require a plurality of steps and screens to be prepared for judging a level of skill. Also, when the screen configuration is prepared in plural or revised to improve operability, a lot of time is taken to modify and verify software. Further, once the software is developed, it is practically hard to add the functions for improving the screen configuration and operability.

Recently, a hierarchical screen configuration allowing the operator to view the overall makeup of operational screens has been employed in many cases. In that case, a job guide is prepared as a document file in another format and is stored in a memory of the same computer or in CD-ROM. Upon a help button being depressed (clicked), a job guidance file is called and displayed as required. Preparing the job guide in another document format separately from the control program software is advantageous in not requiring a long time when the control program software is modified. When the job guide has the search function, the explanation of the objective job can be easily called.

Referring to a paper manual during job is often assistive for the operator to expedite the job. Because the paper manual allows the operator to search for the objective job while looking over the entirety in a table of contents and an index, it is easy to find the objective job. However, when the paper manual is used, the operator has to progress work while alternately looking at operational screens displayed based on application software and the paper manual. Accordingly, the operator is required to move his or her eyes frequently, and working efficiency is deteriorated.

One technique for overcoming the above-described problem with the use of a paper manual is proposed in Patent Document 4 (JP,A 2000-112605). Patent Document 4 discloses a job aid system that, when some button is depressed for a certain time on a screen displayed based on application software, an explanation regarding the screen displayed based on application software at that time is displayed on the same screen.

SUMMARY OF THE INVENTION

However, when the job guide is prepared in another document format separately from the control program software, the following problem occurs. Usually, the job guide is called when some question or something difficult to understand comes out during the progress of job. Therefore, two windows have to be displayed concurrently so that the operator can progress the job while looking at the help window. In general, an active window is displayed on the most front side of superimposed windows displayed in the screen. For that reason, when the operator is going to progress the job based on the control program software after referring to the help window, the held screen displayed at that time must be closed. If the objective screen necessary for continuing the job is not displayed when the held screen is closed, the operator must start work to find out the objective screen.

In particular, when condition setting parameters and information both necessary for performing analysis are inputted over a plurality of operational screens, or when a beginner or an operator temporarily using the control program software performs the job, a longer time is taken until start of the intended operation. Further, when the job is performed over a plurality of operational screens, the operator may sometimes fail to reach the final target because of no navigation.

It is conceivable to change a mode of screen display and operability of the job application software, for example, by changing the screen configuration depending on each level of skill or by displaying navigation in the case of a particular job. Such a solution, however, requires a lot of time and labor for modification of the software.

In many cases, setting of test items, etc. in an analysis device is not so frequently performed once set. However, when change of the setting is necessitated after the lapse of a certain term from the initial setting, in particular when the operator in charge of the relevant analysis is relocated, it is often difficult to understand from which one of the operational screens the job should be started, or what kind of matter should be set.

An object of the present invention is to realize an analysis device allowing any person to utilize job guidance for setting and assignment operations with high efficiency regardless of a level of skill in an automatic analysis device which has a complicated screen configuration with an increase of functions.

To achieve the above object, in an automatic analysis device of the present invention, a storage unit of the automatic analysis device previously stores a correspondence list indicating correspondences between screen IDs for control program software of the automatic analysis device and procedure IDs, keys, codes, buttons, etc. in a job guidance file. When one of the procedures ID or the likes in the job guidance file is selected in a state where the job guidance file independently stored in the storage unit is displayed in a display unit, the screen ID corresponding to the selected procedure ID or the like is searched for in the correspondence list. After a job guidance window is closed, the displayed screen is shifted to one corresponding to the searched screen ID.

According to the present invention, since a document file for job guidance and a control program on the analysis side are independent of each other, the operator can be reliably guided to the objective job screen without changing the configuration of operational screens for the control program on the analysis side. Also, the operator can be reliably guided to the objective job screen by effectively utilizing a paper manual. It is hence possible to increase the efficiency of setting and assignment operations in the complicated automatic analysis device.

Further, operability in, for example, setting the functions, which are not usually performed, can be efficiently increased by storing screen shift processes performed in the past and calling the stored past screen shift processes as required.

BRIEF DESCRIPTION OF THE DRAWINGS

FIG. 3 is a table showing one example of a correspondence list file for shift from a screen based on device control program software to a job guidance window in the automatic analysis device according to the first embodiment of the present invention;

FIG. 4 is a table showing one example of a correspondence list file for shift from procedure IDs in a job guidance file to screen IDs based on the control program software in the automatic analysis device according to the first embodiment of the present invention;

FIG. 8 is a table showing one example of a correspondence list file for shift from procedure IDs in a job guidance file to a screen based on the device control program software in an automatic analysis device according to a third embodiment of the present invention;

DESCRIPTION OF THE PREFERRED EMBODIMENTS

Embodiments of the present invention will be described below with reference to the drawings.

A first embodiment of the present invention will be described below with reference to FIGS. 1-5.

Figure 1:
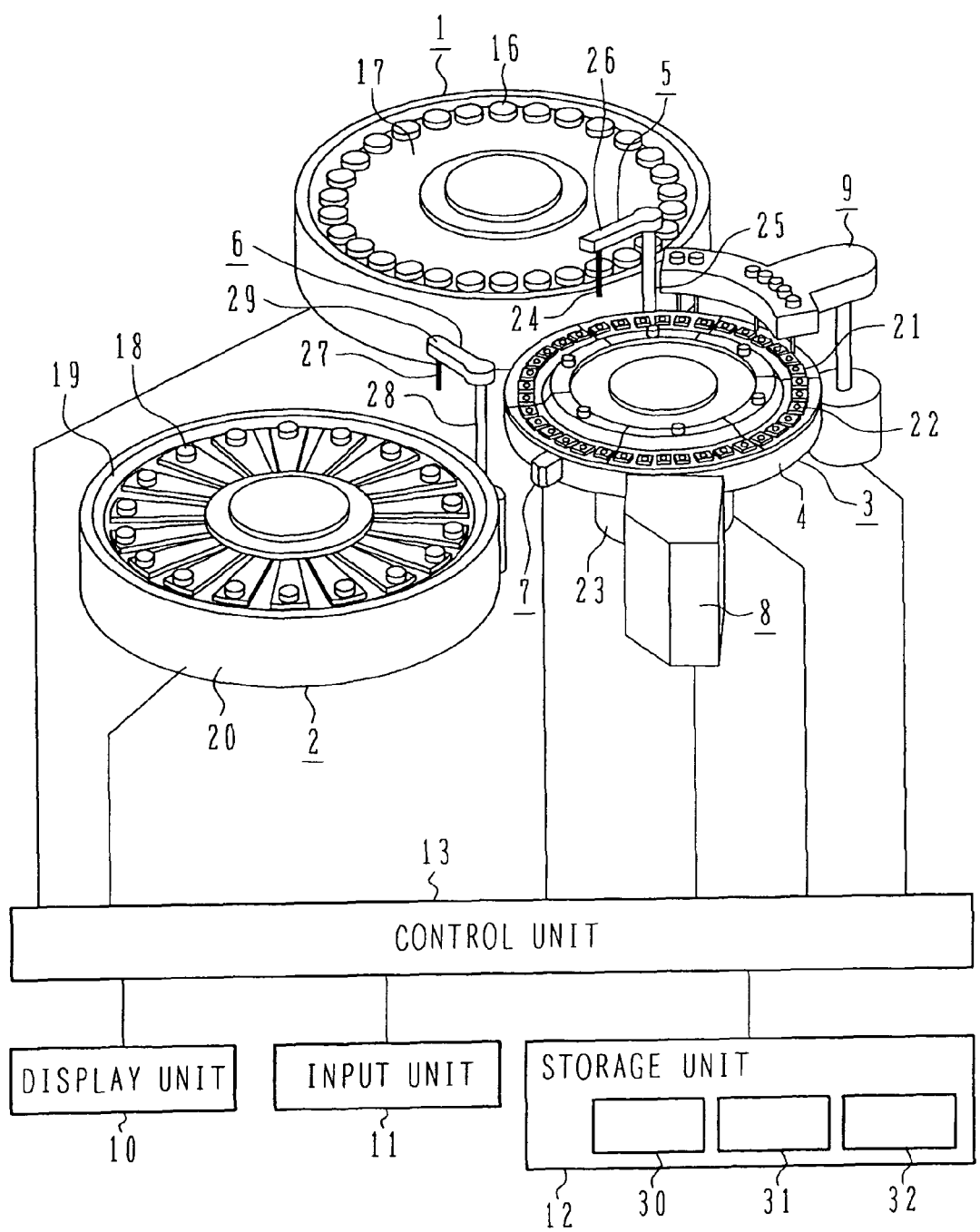
FIG. 1 is a schematic view of an automatic analysis device to which the present invention is applied.

FIG. 1 is a schematic view of an automatic analysis device to which the present invention is applied.

In FIG. 1, the automatic analysis device according to the first embodiment of the present invention comprises mainly a sample disk 1, a reagent disk 2, a reaction disk 3, an incubator bath 4, a sampling mechanism 5, a pipetting mechanism 6, a mixing mechanism 7, a photometry mechanism 8, a washing mechanism 9, a display unit 10, an input unit 11, a storage unit 12, and a control unit 13.

On the sample disk 1, a plurality of sample cups 16 containing extracted samples are fixedly arranged along the circumference of a circular disk 17. The circular disk 17 is rotated in the circumferential direction and is stopped in a predetermined position by a driving mechanism constituted by, e.g., a motor and a rotary shaft (not shown).

On the reagent disk 2, a plurality of reagent bottles 18 containing reagents to be mixed in the samples for reaction are fixedly arranged along the circumference of a circular disk 19. The reagent bottles 18 are surrounded by a cool box 20 under temperature control.

The circular disk 19 is rotated in the circumferential direction by a driving mechanism constituted by, e.g., a motor and a rotary shaft (not shown) in such a manner that the circular disk 19 can be positioned in any desired location.

On the reaction disk 3, a plurality of reaction cuvette holders 22 are mounted which hold reaction cuvettes 21 for receiving samples and reagents. The reaction disk 3 is driven by a driving mechanism 23 so as to repeatedly start and stop rotation in the circumferential direction at a certain cycle, whereby the reaction cuvettes 21 are intermittently transferred.

The incubator bath 4 is installed in a path of movement of the reaction cuvettes 21. The incubator bath 4 is installed to promote chemical reaction between the samples and reagents and is filled with, e.g., incubator water under temperature control. The reaction cuvettes 21 are moved within the incubator bath 4, and reaction liquids in the reaction cuvettes 21 are controlled to be held at a constant temperature.

The sampling mechanism 5 comprises a support shaft 25, an arm 26 mounted to the support shaft 25, a probe 24 mounted to a fore end of the arm 26, and a driving mechanism (not shown) for reciprocally moving the probe 24 between the sample disk 1 and the reaction disk 3 with the support shaft 25 serving as a center of rotation.

In accordance with a preset sequence, the sampling mechanism 5 supplies, to the reaction cuvette 21 on the reaction disk 3, the sample in the sample cup 16 which is transferred to the predetermined position with the rotation of the sample disk 1.

Similarly to the sampling mechanism 5, the pipetting mechanism 6 comprises a support shaft 28, an arm 29 mounted to the support shaft 28, a probe 27 mounted to a fore end of the arm 29, and a driving mechanism (not shown) for reciprocally moving the probe 27 between the reagent disk 2 and the reaction disk 3 with the support shaft 28 serving as a center of rotation.

In accordance with a preset sequence, the pipetting mechanism 6 supplies, to the reaction cuvette 21 on the reaction disk 3, the reagent in the reagent bottle 18 which is transferred to the predetermined position with the rotation of the reagent disk 2.

Different kinds of samples and reagents are put in the sample cups 16 and the reagent bottles 18, respectively. Each sample and each reagent are supplied in respective required amounts to the corresponding reaction cuvette 21.

The display unit 10 is constituted by a CRT display or a liquid crystal monitor on which various screens representing analysis items, analysis results, etc. are displayed. Also, the input unit 11 is used for inputting various kinds of information, such as the analysis items. The storage unit 12 is provided in a personal computer installed in the operating section. The storage unit 12 stores a preset sequence (program) for controlling the various mechanisms and various kinds of information, such as the analysis items, which are represented by device control program software 30, a job guidance file 31, and a correspondence list file 32 indicating correspondences between screen IDs and procedure IDs, codes, buttons, etc. in the job guidance file 31 (hereinafter collectively referred to as "procedure IDs or the likes").

The storage unit 12 may comprise two memories, i.e., a memory inside the analysis device and a memory inside the personal computer installed in the operating section. In this case, the memory inside the analysis device is always communicated with the memory inside the personal computer installed in the operating section via a communication cable for transfer of information.

In addition to the components shown in FIG. 1, the automatic analysis device according to the first embodiment of the present invention includes other components, such as a syringe and a pump. All of the components including those other components are controlled by the control unit 13 in accordance with the sequence stored in the storage unit 12.

Figure 2:
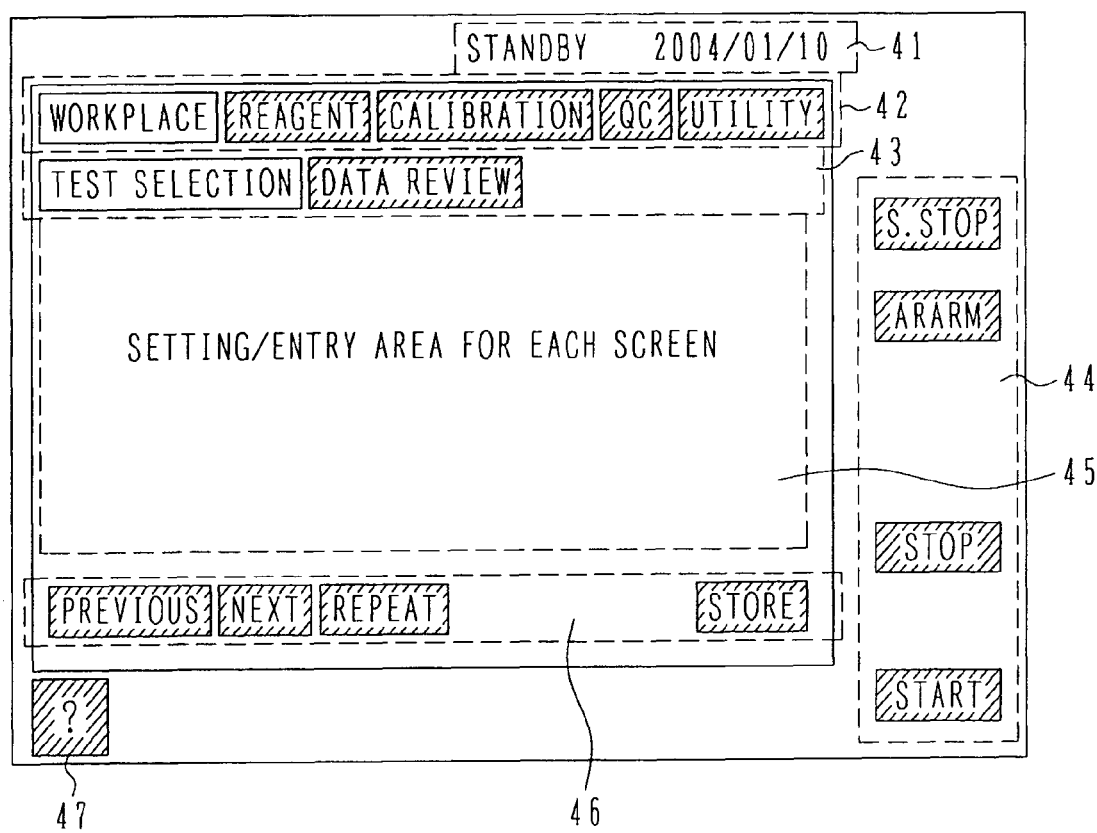
FIG. 2 is an illustration showing one example of an operational screen of an automatic analysis device according to a first embodiment of the present invention.

FIG. 2 is an illustration showing one example of an operational screen of an automatic analysis device according to the first embodiment of the present invention.

As shown in FIG. 2, tabs for a job menu 42 and a sub-job menu 43 are always displayed on an operational screen. The screen is shifted from one to another upon selection of any desired tab.

Also, the operational screen includes a status display area 41 for displaying the device status, date, etc., a global menu area 44 used for commanding start and stop of measurement to the analysis device, a setting/entry display area 45 for each screen, a group of functions buttons 46 for making shift from each screen to window display, and a help button (particular key) 47 for displaying a help file. Thus, the operational screen is displayed in such a layout that an operator is able to view the entirety of the device functions and manage the state of the analysis section.

FIG. 3 is a table showing one example of a correspondence list file 32 indicating correspondences between screen IDs based on the device control program software 30 and procedure IDs or the likes in the job guidance file 31 in the automatic analysis device according to the first embodiment of the present invention. The correspondence list file 32 for shift from a screen based on the device control program software 30 to a job guidance window includes individual screen IDs and corresponding help file IDs.

The operational screen displayed as shown in FIG. 2 has a hierarchical structure made up of a major job menu (e.g., workplace) at a top level, a sub-menu (e.g., test selection and data review) at a next level, and windows (e.g., demographics and repeat). Although the tabs for the job menu 42 and the sub-job menu 43 are always displayed in the operational screen of FIG. 2, the windows are displayed as function buttons representing respective menu screens. In some cases, further windows are present at a level lower than the displayed windows.

The correspondence list file 32 of FIG. 3 is a correspondence table in which an ID is assigned to each of the screens and windows, and an ID for the job guidance file to be displayed correspondingly (i.e., a help file ID) is set in one-to-one relation to the screen ID.

For example, it is assumed that the help button 47 is depressed in the state of a demographics screen being displayed on a test selection screen for the workplace job. In such a case, because a demographics screen ID is "HDY¥Work¥Demo" as shown in FIG. 3, the control unit 13 outputs a command for instructing a corresponding help file, i.e., a help file A_1_1, to be displayed in the display unit 10.

Note that the above-described correspondence is also performed in a known method for displaying a job guidance screen. In this embodiment, the following description is made of a manner for making shift from the job guidance window to the screen according to the device control program software 30.

FIG. 4 is a table showing one example of the correspondence list file 32 indicating correspondences between the procedure IDs or the likes in the job guidance file 31 and the screen IDs based on the device control program software 30.

The correspondence list file 32 is stored in the storage unit 12 such that, as shown in FIG. 4, the screen IDs based on the device control program software 30 are made correspondent to the procedure IDs or the likes in one-to-one relation. When any one of the procedure IDs or the likes is selected while the job guidance is displayed, the corresponding application screen ID is temporarily stored in the storage unit 12.

For example, when the operator cannot understand a manner of assigning a sample to be measured again to a rerun rack and selects "Rerun rack assignment" in the column "Name of procedure" on the help screen, a search is made in the correspondence list file 32 stored in the storage unit 12. Based on the correspondence shown in FIG. 4, the screen ID "HD¥Work¥rerun" corresponding to the procedure ID of "Rerun rack assignment", i.e., "Rerun_Rack_regist", is temporarily stored in the storage unit 12.

Subsequently, when the job guidance window is closed, the displayed screen is returned to the screen based on the control program software 30. At that time, control is executed such that the above-mentioned screen ID having been temporarily stored in the storage unit 12 is called and the operational screen corresponding to the called screen ID is displayed in the display unit 10.

Even in the case of the job guidance window being closed at timing optionally selected, if any screen ID is temporarily stored, the operational screen corresponding to the stored screen ID is displayed in the display unit 10.

Figure 5:
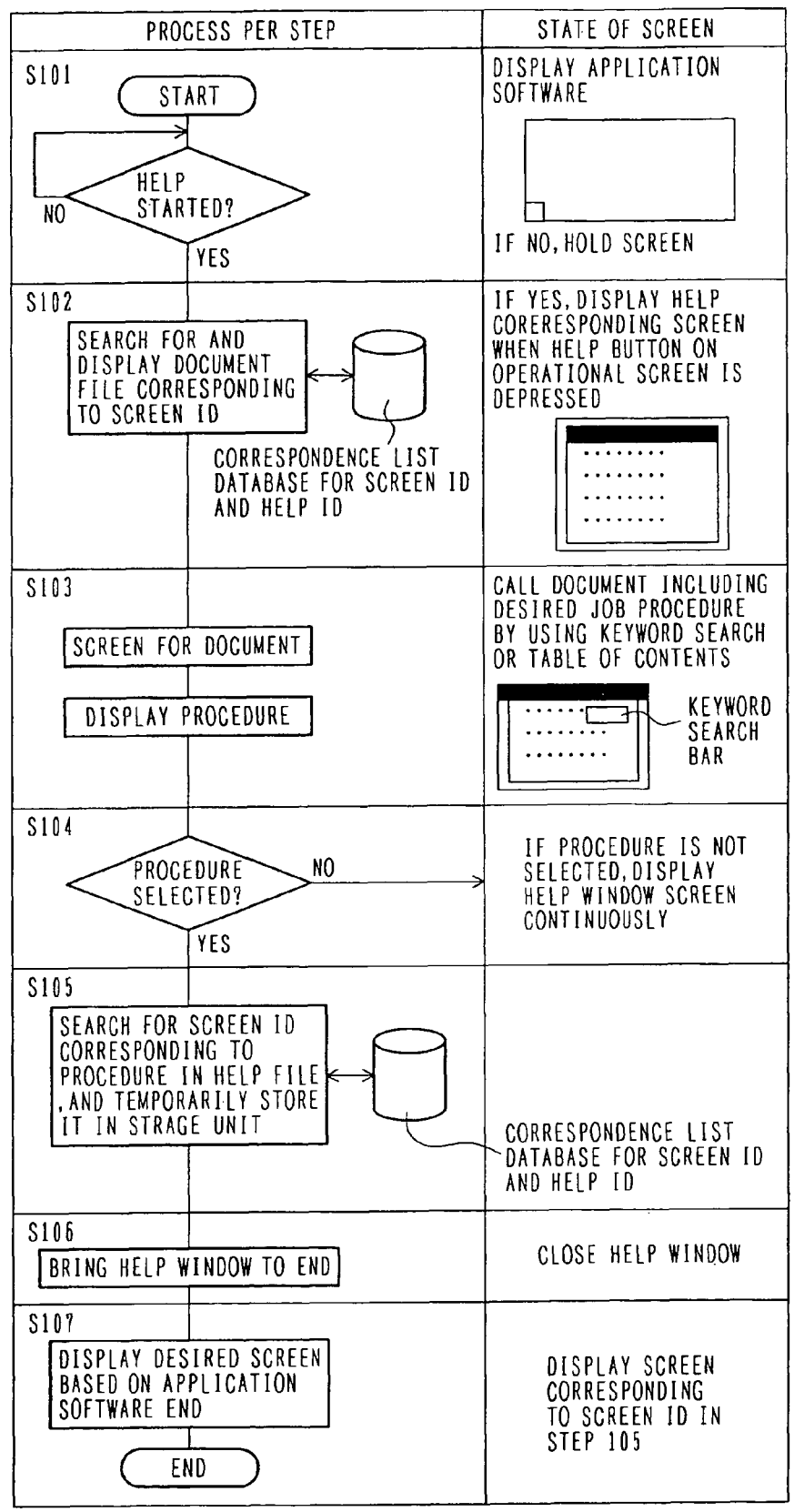
FIG. 5 is a process flowchart for screen shifting in the automatic analysis device according to the first embodiment of the present invention.

FIG. 5 is a process flowchart for screen shifting in the automatic analysis device according to the first embodiment of the present invention.

In step S101 of FIG. 5, the analysis device is powered on and an application program is started to display the operational screen of the job guidance file 31 in the display unit 10.

If the help button 47 is not depressed at that time, the operational screen is displayed based on the device control program software 30.

If the help button 47 is depressed in step S101, the help file ID corresponding to the screen ID is searched for in the correspondence list file 32 shown in FIG. 3, and the window of the corresponding help file ID is displayed (step S102).

Thereafter, in a job guidance document, the job procedure to be performed is searched for and displayed by using a table of contents or a keyword (step S103). It is here determined whether the procedure ID or the like in the window of the job guidance file 31 is selected (step S104). If the procedure ID or the like is not selected, the help window is continuously displayed as it is. The procedure ID or the like may be any of a viewable key, ID, code, name, etc. in the screen so long as it can be visually recognized when selected. Preferably, the job guidance file 31 has the procedure list display function for the purpose of higher efficiency.

At the same time as when the procedure ID or the like in the job guidance file 31 is selected, the screen ID based on the device control program software 30, which corresponds to the procedure ID or the like, is searched for in the correspondence list file 32 and the searched screen ID is temporarily stored in the storage unit 12 (step S105).

Then, the window of the job guidance file 31 is closed (step S106). Simultaneously, the screen ID based on the device control program software 30, which corresponds to the stored screen ID, is displayed (step S107).

According to the first embodiment of the present invention constituted as described above, since a document file for job guidance and a control program on the analysis side are independent of each other, the operator can be reliably guided to the objective job screen without changing the configuration of the operational screens for the control program on the analysis side, i.e., with no need of modifying the operational screens or making the screens adapted for navigation display depending on a level of each operator, while utilizing the help display function to the utmost. It is hence possible to increase the efficiency of setting and assignment operations in the complicated automatic analysis device.

A second embodiment of the present invention will be described below with reference to FIGS. 6 and 7.

The automatic analysis device according to the second embodiment of the present invention utilizes convenience of a manual in the form of paper or sheets. The manual in the form of paper or sheets is prepared instead of the job guidance file 31 stored in the storage unit 12. The other construction is the same as that in the automatic analysis device according to the first embodiment of the present invention.

Figure 6:
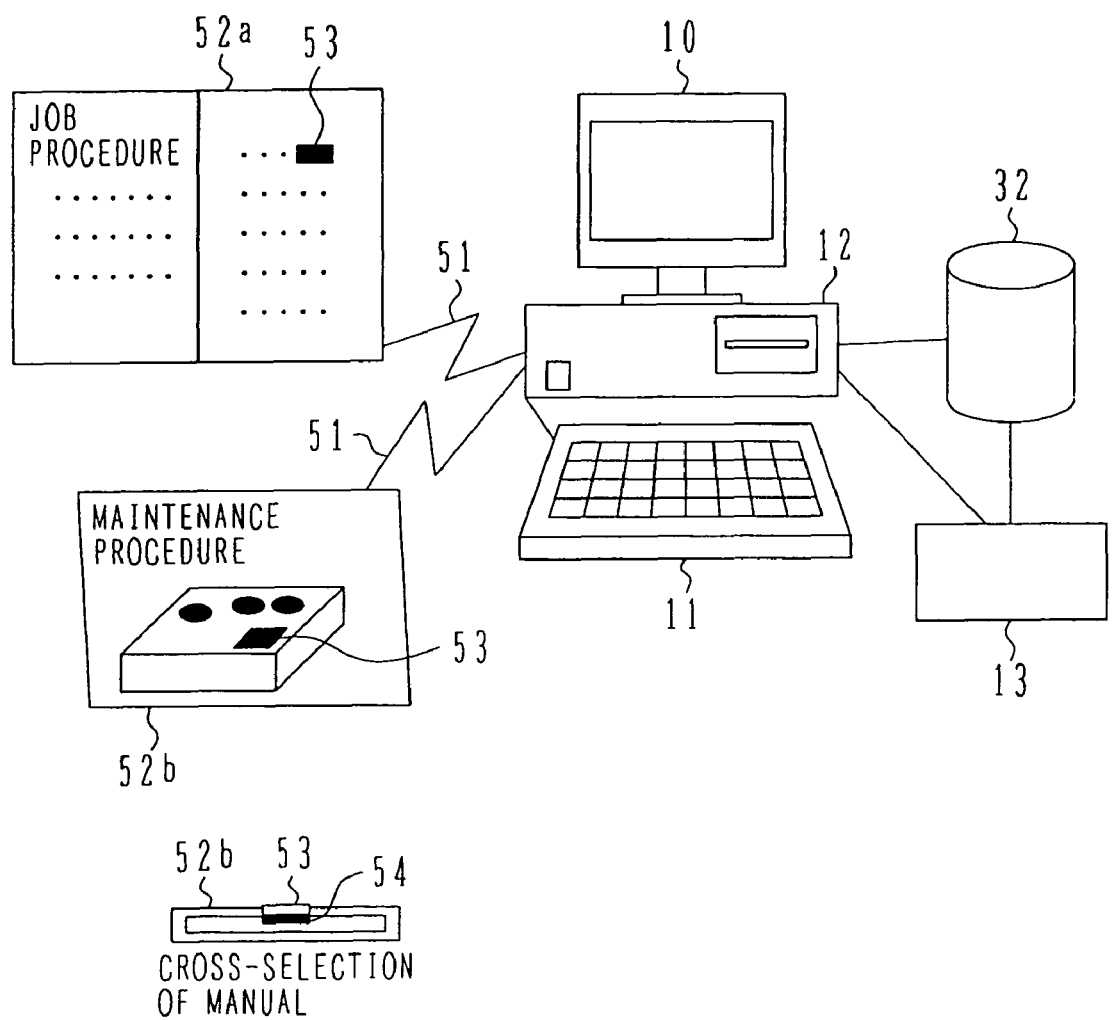
FIG. 6 is an illustration showing the relationship between a manual and the whole of an operating section in an automatic analysis device according to a second embodiment of the present invention.

FIG. 6 illustrates the relationship between a manual 52 (52a, 52b) and the whole of an operating section in the automatic analysis device according to the second embodiment of the present invention.

In FIG. 6, the automatic analysis device according to the second embodiment of the present invention comprises the manual 52, the operating section, and a control unit 13. The operating section comprises a display unit 10, a storage unit 12, and an input unit 11. The storage unit 12 of the operating section is connected to the control unit 13, and the control unit 13 controls the input unit 11 and the display unit 10.

The manual 52 is provided as a paper manual or a simplified sheet manual 52a explaining how to handle the analysis device, e.g., how to proceed jobs, or as a manual 52b for maintenance and check of the analysis device. In particular, maintenance operations to be performed for maintenance and check of the analysis device are also preferably stored in the form of individual procedures so that the operational screen can be shifted to a maintenance screen based on the maintenance manual.

The manual 52 is connected to the storage unit 12 and the control unit 13 via communication means 51. The communication means 51 are preferably constituted as, e.g., communication cable connection or infrared communication used for remote control.

The storage unit 12 stores device control program software 30, the manual 52, and a correspondence list file 32 indicating correspondences between procedure IDs (ID keys) 53 in the manual 52 and screen IDs based on the device control program software 30. One example of the correspondence list file 32 is the same as the list file shown in FIG. 4.

In a part of the manual 52, a sensor 54, e.g., an IC for sensing selection of the procedure ID 53, is previously built in each of a plurality of job guidance items in one-to-one relation. When the sensor 54 is depressed, a signal representing the depression of the senor 54 is transmitted to the storage unit 12 via the communication means 51. In other words, when the operator refers to the manual 52 and selects the objective procedure ID 53 by using an index, a table of contents, etc., the selection of the objective procedure ID 53 is informed to the control unit 13 via the communication means 51.

If the selection of the procedure ID 53 or the like in the manual 52 is transmitted to both the storage unit 12 and the control unit 13 via the communication means 51, the operational screen based on the device control program software 30, which corresponds to the selected procedure ID 53 or the like, is displayed.

Figure 7:
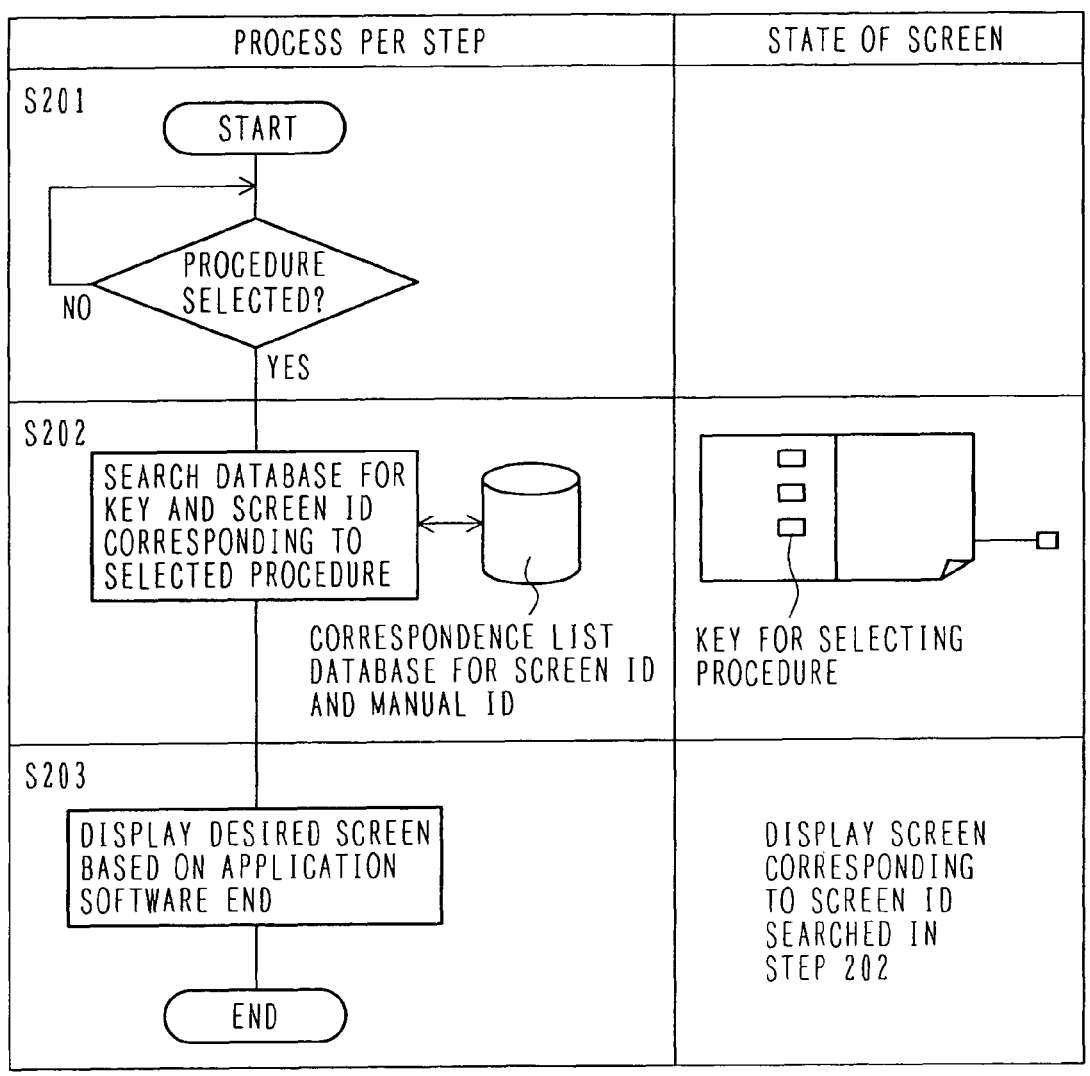
FIG. 7 is a process flowchart for screen shifting in the automatic analysis device according to the second embodiment of the present invention.

FIG. 7 is a process flowchart for screen shifting in the automatic analysis device according to the second embodiment of the present invention.

In step S201 of FIG. 7, the analysis device is powered on and the device control program software 30 is started to display an operational screen in the display unit 10. In this state, the procedure ID 53 or the like in the manual 52 is selected. If the procedure ID 53 or the like is not selected in that state, the operational screen based on the device control program software 30 is displayed.

If the procedure ID 53 or the like is selected in step S201, the corresponding screen ID based on the device control program software 30 is simultaneously searched for in the correspondence list file 32 stored in the storage unit 12 (step S202). The selected procedure ID 53 or the like may be any of a viewable key, ID, code, name, etc. in the screen so long as it can be visually recognized when selected.

Then, the operational screen is shifted to one based on the device control program software 30, which corresponds to the searched screen ID, and is displayed (step S203).

According to the second embodiment of the present invention constituted as described above, by effectively utilizing a manual in the form of paper or sheets, the operator can be reliably guided to the objective job screen without changing the configuration of the operational screens for the control program on the analysis side, i.e., with no need of modifying the operational screens or making the screens adapted for navigation display depending on a level of each operator, while utilizing the help display function to the utmost. It is hence possible to increase the efficiency of setting and assignment operations in the complicated automatic analysis device.

A third embodiment of the present invention will be described below with reference to FIGS. 8 and 9.

FIG. 8 is a table showing one example of a correspondence list file including grouped screen IDs and grouped procedure IDs, i.e., grouped procedure IDs or the likes in a job guidance file 31, in an automatic analysis device according to the third embodiment of the present invention.

In the automatic analysis devices according to the first and second embodiments of the present invention, objective job procedures have to be often performed over a plurality of operational screens. In such a case, the procedure IDs in the job guidance file or the manual and the screen IDs do not correspond to each other in (1:1) relation. The third embodiment of the present invention enables the procedure IDs to be assigned in groups to be adapted for the above case.

Similarly to the correspondence list file 32 in the first embodiment of the present invention shown in FIG. 3 or 4, a correspondence list file 32a indicating correspondences between respective group IDs of procedure IDs and the screen IDs is prepared as shown in FIG. 8. Each group ID is expressed in such a manner as enabling the operator to recognize the presence of a plurality of screen IDs. On that occasion, the first operational screen is displayed as one corresponding to the top screen ID in the group, and the screen IDs are all temporarily stored as one group in the storage unit 12.

If the window of the job guidance file 31 is closed or the procedure ID 53 or the like in the manual 52 is selected, the operational screen based on the device control program software 30 is displayed such that the screen corresponding to the top screen ID in the group ID, which has been temporarily stored in the storage unit 12, is called and displayed in the display unit 10.

Figure 9:
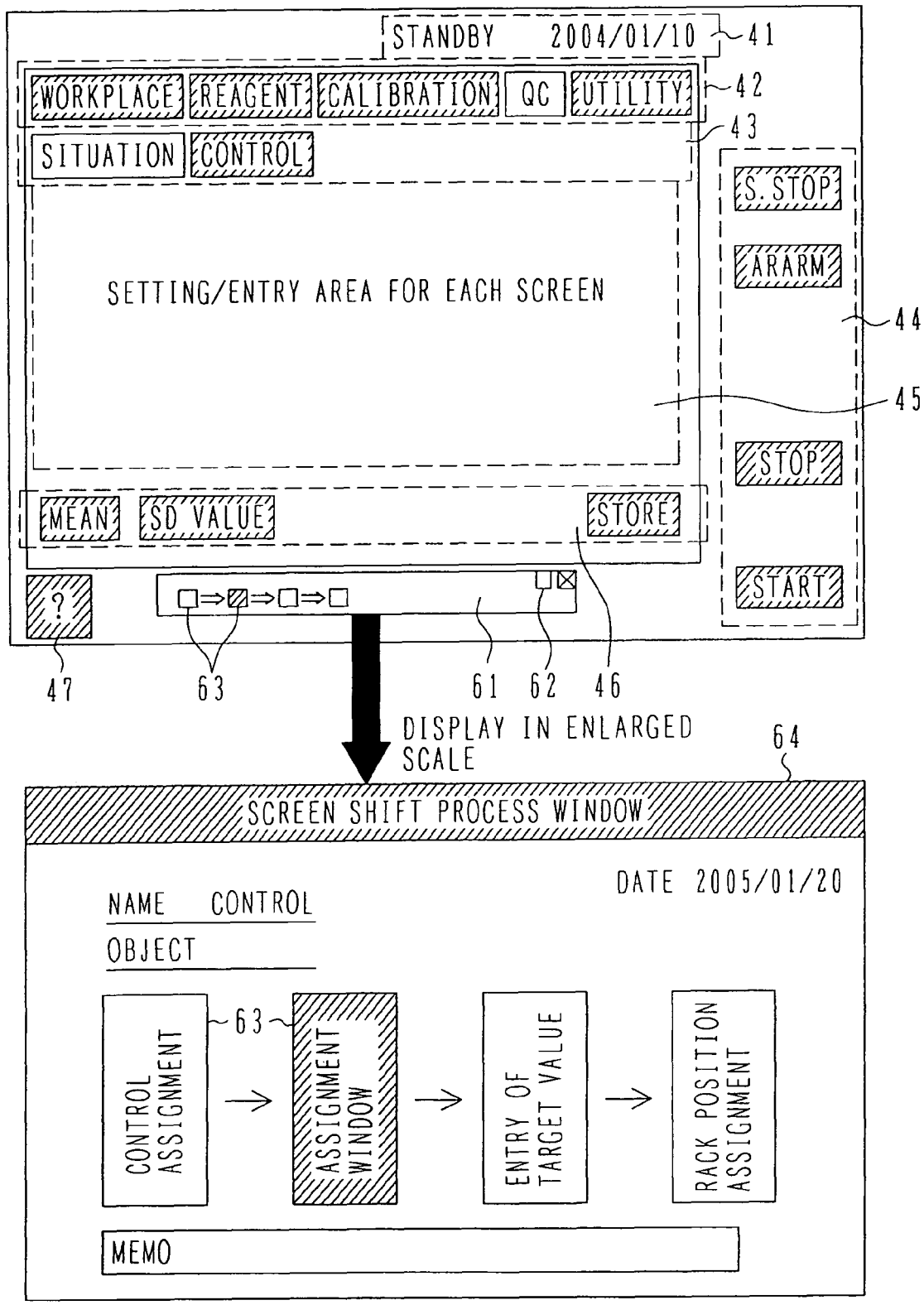
FIG. 9 is an illustration showing one example of a screen-shift process display screen in the automatic analysis device according to the third embodiment of the present invention.

FIG. 9 is an illustration showing one example of a screen-shift process display screen in the automatic analysis device according to the third embodiment of the present invention.

In grouped screen shift processes, as shown in FIG. 9, a simplified display window 61 is disposed in the screen. The simplified display window 61 displays the sequence of the screen shift processes and the process currently under run in a manner recognizable by the operator. In the example of FIG. 9, the color of an icon representing the process currently under run is reversed so that the operator can recognize the process currently under run. When one of process buttons 63 indicated in the process flow is selected or when the display of the current screen is brought to an end, the screen is shifted to another one representing the next process. The process buttons 63 are optionally selectable regardless of the button order in the flow of the screen shift processes. When the operator wants to look detailed information, a screen shift process window 64 is displayed by depressing an enlarged display button 62.

The screen shift process window 64 displays the title of the screen shift process window, the date of setting performed in the past, and the name and object of the screen. When the process button 63 is depressed, the displayed procedure is advanced to next one. The operator can enter the object and memo in screen shift process window 64 so that working efficiency can be increased when another operator performs the similar job later.

As with the simplified display window 61, when the process button 63 is selected or when the display of the current screen is brought to an end, the screen is shifted to another one representing the next process. By optionally selecting the process button 63, it is also possible to skip intermediate processes in the course until reaching the objective process. When the display of the final screen is brought to an end, the screen shift process window 64 is erased.

According to the third embodiment of the present invention constituted as described above, the operator can be reliably guided to the objective job screen even when the objective job procedures have to be performed over a plurality of operational screens. It is hence possible to increase the efficiency of setting and assignment operations in the complicated automatic analysis device.

A fourth embodiment of the present invention will be described below with reference to FIGS. 10 and 11.

The automatic analysis device according to the fourth embodiment of the present invention additionally has the function of, when a procedure not included in the manual 52 or the job guidance file 31 is needed, newly assigning a corresponding screen shift process in the device control program software 30.

Figure 10:
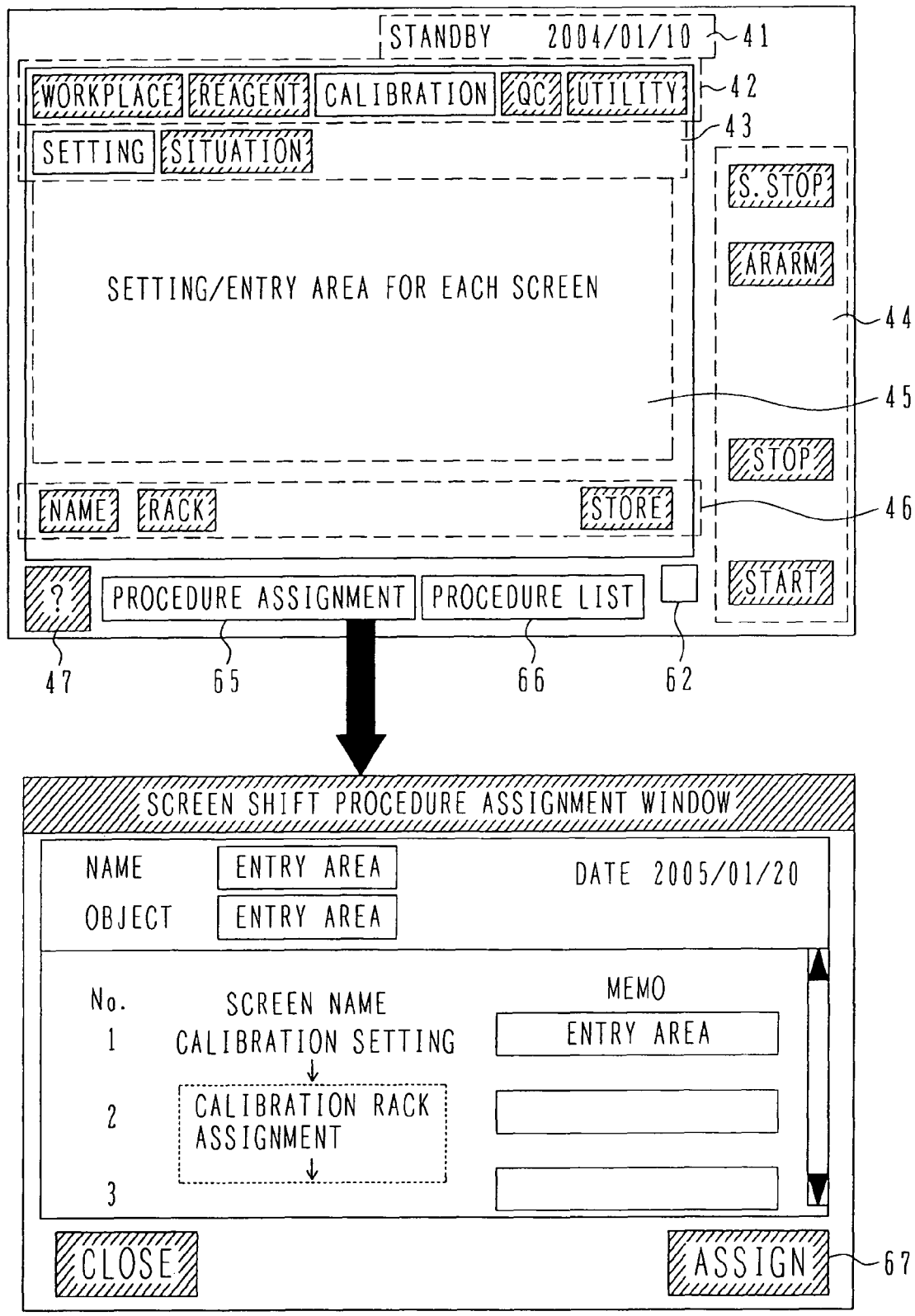
FIG. 10 is an illustration showing one example of a screen-shift process assignment screen in an automatic analysis device according to a fourth embodiment of the present invention.

FIG. 10 is an illustration showing one example of a screen-shift process assignment screen in the automatic analysis device according to the fourth embodiment of the present invention.

In FIG. 10, when the operator selects a procedure assignment button 65 in the screen, a procedure assignment window 65 is displayed.

The procedure assignment window 65 displays the name, object and number of the procedure, and a memo entry box in which what has been performed in the past is entered for each screen. When an assignment button 67 is depressed in the state of information being entered in each entry box and of particulars to be assigned being displayed in the screen, the ID of the displayed screen is searched by the device control program software 30. Then, the searched screen ID is assigned after displaying the screen name. By repeating those operations in sequence at required number of times corresponding to the procedures to be assigned, screen shift procedures are assigned.

Figure 11:
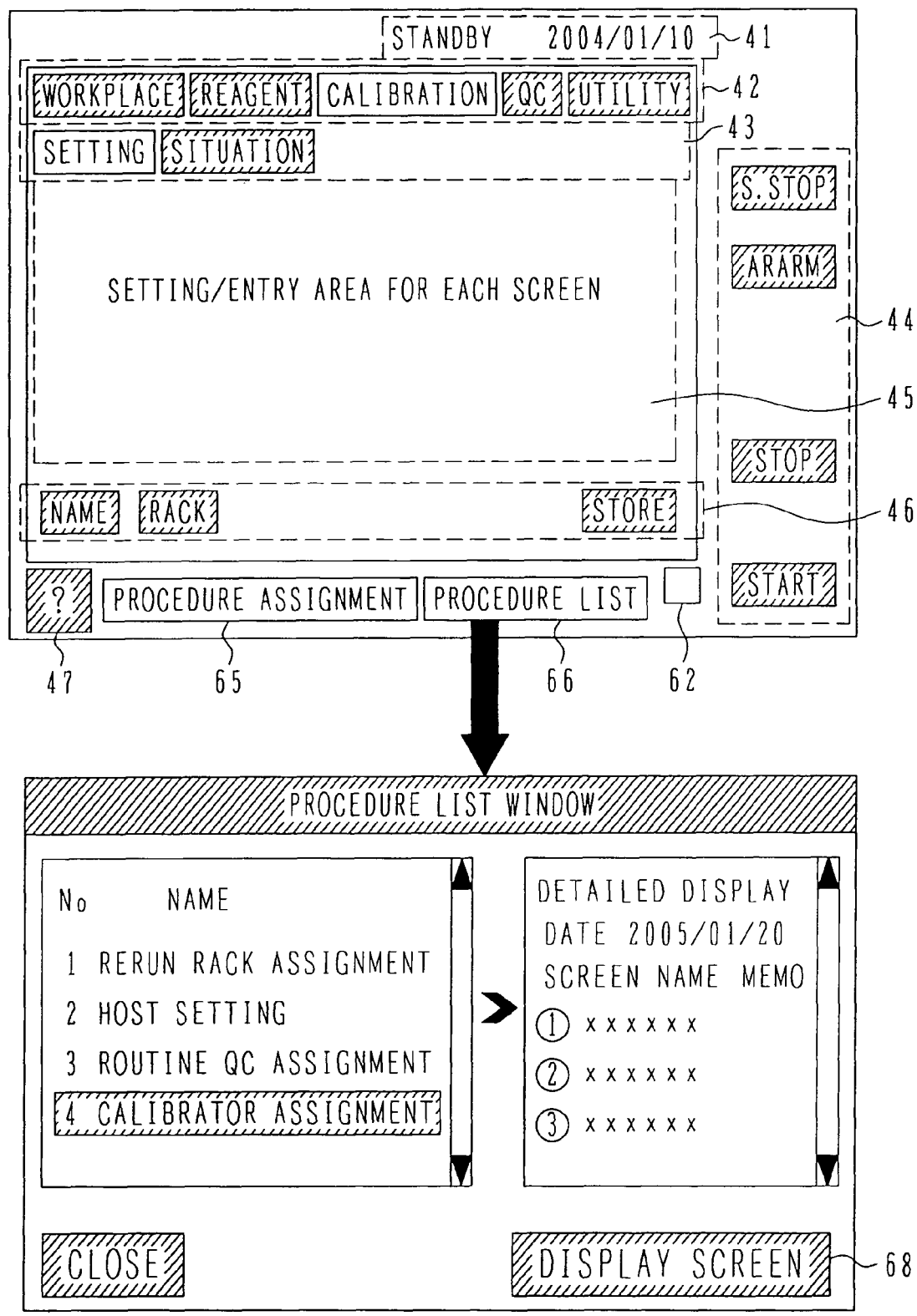
FIG. 11 is an illustration showing one example of a screen for displaying screen shift processes assigned in the automatic analysis device according to the fourth embodiment of the present invention.

FIG. 11 is an illustration showing one example of a screen for displaying screen shift processes assigned in the automatic analysis device according to the fourth embodiment of the present invention.

In FIG. 11, when the operator selects a procedure list button 66 in the screen, a procedure list window is displayed.

The procedure list window displays, on its left side, a procedure list and, on its right side, detailed information of the selected item in the procedure list on the left side. Further, a screen display button 68 is displayed at a lower right corner of the window. When the screen display button 68 is selected in the state of the detailed information being displayed on the right side of the window, the screen is shifted to the screen representing the selected procedure list. In that case, the simplified display window 61 described above in the third embodiment of the present invention with reference to FIG. 9 is displayed. Further, as in the screen of FIG. 9, the screen shift process window 64 can be displayed by depressing the enlarged display button 62.

According to the fourth embodiment of the present invention constituted as described above, operability in setting the functions, which are not usually performed, can be efficiently increased by storing the screen shift processes performed in the past and calling the stored past screen shift processes as required.

The above description has been made in connection with the embodiments in which the present invention is applied to the automatic analysis device. However, the present invention is not limited to the automatic analysis device, and it is also applicable to other devices each of which has the complicated functions, requires a plurality of operational screens for setting and maintenance operations, and employs a personal computer in the operating section.

What is claimed is:

1. An analysis device comprising an analysis unit for analyzing a sample, a storage unit for storing plural kinds of device control program information for said analysis unit and corresponding job guidance information, a display unit for displaying the plural kinds of device control program information and the job guidance information, and a control unit configured to control said analysis unit, said storage unit and said display unit, wherein the plural kinds of device control program information stored in said storage unit are provided with respective identification symbols and the job guidance information is stored in said storage unit corresponding to the identification symbols;

said control unit is configured to control said display unit to display one kind of device control program information selected by an operator from among said plural kinds of device control program information along with a specific key, and when the displayed specific key is manipulated by the operator, said control unit is configured to store the identification symbol of the one kind of device control program information selected by the operator in said storage unit and change said display unit to display the job guidance information corresponding to the stored identification symbol;

when the operator, while the job guidance information is displayed, selects a procedure explained in the displayed job guidance information, the control unit is configured to store into the storage unit the identification symbol of another kind of device control program information which corresponds to the selected procedure; and when the operator instructs the end of display of the job guidance information, said control unit is further configured to change said display unit to display the another kind of device control program information which corresponds to the selected procedure with the identification symbol stored in said storage unit and which differs from the one kind of device control program information displayed before the specific key is manipulated.

2. The analysis device according to claim 1, wherein the job guidance information is divided into groups of information, each group containing plural kinds of job guidance information;

the plural kinds of device control program information stored in said storage unit are given with respective identification symbols, the identification symbols being divided into groups each having group information stored in said storage unit; and when the operator instructs the end of display of the job guidance information, said control unit is configured to display, in said display unit, the device control program information with the identification symbol corresponding to the group information of the grouped identification symbols, which has been stored in said storage unit.

3. The analysis device according to claim 2, wherein a window allowing the operator to recognize screen shift processes corresponding to the group information of the grouped identification symbols is displayed in an operational screen based on a device control program such that the operator is able to recognize the process currently under run and to optionally select a desired process.

4. The analysis device according to claim 1, wherein said control unit is further configured to store associated information, including date, name and object of each screen shift process whenever the screen shift process is performed, such that the past screen shift processes can be reproduced as required.

5. An analysis device comprising an analysis unit for analyzing a sample, a storage unit for storing plural kinds of device control program information for said analysis unit, a display unit for displaying the plural kinds of device control program information, and a control unit configured to control said analysis unit, said storage unit and said display unit, wherein said display unit displays one kind of the plural kinds of device control program information;

said analysis device includes manual means containing job guidance information and having identification keys assigned respectively to job explanation items in the job guidance information;

the plural kinds of device control program information are stored in said storage unit corresponding to the identification keys in said manual means;

said manual means includes sensors disposed corresponding to the job explanation items in the job guidance information and sensing manipulations of the identification keys, respectively; and when any of said sensors senses the manipulation of any of the identification keys disposed in said manual means, said control unit is configured to display, in said display unit, the device control program information stored in said storage unit corresponding to the manipulated identification key which differs from the one kind of the plural kinds of device control program information.

6. The analysis device according to claim 5, wherein the job guidance information is divided into groups of information, each group containing plural kinds of job guidance information;

the plural kinds of device control program information stored in said storage unit are given with respective identification symbols, the identification symbols being divided into groups each having group information stored in said storage unit; and when the operator instructs the end of display of the job guidance information, said control unit is configured to display, in said display unit, the device control program information with the identification symbol corresponding to the group information of the grouped identification symbols, which has been stored in said storage unit.

7. The analysis device according to claim 5, wherein said control unit is further configured to store associated information, including date, name and object of each screen shift process whenever the screen shift process is performed, such that the past screen shift processes can be reproduced as required.

* * * * *